United States Patent [19]

Dean et al.

[11] Patent Number: 5,218,128
[45] Date of Patent: Jun. 8, 1993

[54] BIFUNCTIONAL COUPLING AGENTS AND RADIONUCLIDE LABELED COMPOSITIONS PREPARED THEREFROM

[75] Inventors: Richard T. Dean, Downington, Pa.; Raymond H. Boutin, Wilmington, Del.; Robert W. Weber, Downington, Pa.

[73] Assignee: Centocor, Inc., Malvern, Pa.

[21] Appl. No.: 207,261

[22] Filed: Jun. 15, 1988

[51] Int. Cl.$^5$ .................. C07D 207/40; C07C 327/00
[52] U.S. Cl. .................... 548/546; 558/254; 564/153; 564/154
[58] Field of Search ................ 424/85; 558/254; 564/153, 154; 548/546

[56] References Cited

U.S. PATENT DOCUMENTS

| | | | |
|---|---|---|---|
| 4,287,362 | 9/1981 | Yokoyama et al. | 558/251 |
| 4,421,735 | 12/1983 | Haber et al. | 558/251 |
| 4,659,839 | 4/1987 | Nicoletti et al. | 558/251 |
| 4,668,503 | 5/1987 | Hnatowich | 558/251 |
| 4,670,545 | 6/1987 | Fritzberg et al. | 558/251 |
| 4,671,958 | 6/1987 | Rodwell et al. | 558/251 |
| 4,678,667 | 7/1987 | Meares et al. | 558/251 |

FOREIGN PATENT DOCUMENTS

| | | | |
|---|---|---|---|
| 2109407 | 10/1981 | European Pat. Off. | 558/251 |
| 0137457 | 4/1985 | European Pat. Off. | 558/251 |
| 0173629 | 8/1985 | European Pat. Off. | 558/251 |
| 0188256 | 1/1986 | European Pat. Off. | 558/251 |
| 0248506 | 4/1987 | European Pat. Off. | 558/251 |
| 0250013 | 5/1987 | European Pat. Off. | 558/251 |
| WO87/05030 | 7/1989 | PCT Int'l Appl. | 558/251 |

OTHER PUBLICATIONS

B. A. Khaw et al., *Science*, 209:295–297 (1980).

A. R. Fritzberg, "Radiolabeling of Antibodies with Tc-99 mm Using $N_2S_2$ Ligands," *J. Nucl. Med.* 27: 957–958 (1986).

R. F. Schneider et al., "N,N$^1$-bis(S-Benzoylmercaptoacetamido Ethylenediamine and Propylenediamine Ligands as Renal Function Imaging Agents," *J. Nucl. Med.*, 25(2): 223–229 (1984).

M. W. Brechbiel et al., "Synthesis of 1-(p-Isothiocyanatobenzyl) Derivatives of DTPA and EDTA. Antibody Labeling and Tumor-Imaging Studies," *Inorg. Chem*, 25: 2772–2781 (1986).

*Primary Examiner*—Mary C. Lee
*Assistant Examiner*—Joseph K. McKane
*Attorney, Agent, or Firm*—Hamilton, Brook, Smith & Reynolds

[57] ABSTRACT

A bifunctional coupling agent for joining a sulfhydryl-containing protein or peptide and a metallic radionuclide comprising a sulfhydryl selective electrophile, a chelator containing at least one protected thiol and a organic linking radical which serves to join said electrophile and said chelator is disclosed. A radiodiagnostic precursor comprising an antibody or antibody fragment and the specified bifunctional coupling agent bound to a sulfhydryl group on the antibody or antibody fragment is also disclosed.

1 Claim, No Drawings

BIFUNCTIONAL COUPLING AGENTS AND RADIONUCLIDE LABELED COMPOSITIONS PREPARED THEREFROM

BACKGROUND OF THE INVENTION

Field of the Invention

This invention relates to the fields of radiolabeled proteins and immunodiagnostics and, more particularly, to methods for labelling antibodies and fragments thereof with radiometals.

Background of the Invention

The use of radiolabeled antibodies for the detection of disease states has been recognized as an important advancement in nuclear medicine. The use of monoclonal antibodies should ideally provide new highly specific diagnostic agents. Technetium-99m is regarding as the preferred choice for a gamma emitting scintigraphic agent due to the ease of detection of the emitted photon, as well as its short half-life. Current methods for the attachment of technetium to antibodies have fallen short of the goals of ease of preparation, retention of immunoreactivity, rapid distribution to the target tissue, rapid clearance and no significant localization at sites other than the target.

Two general approaches have been taken to radiolabel proteins. The first is the direct labeling method by which the radiometal is bound to the protein molecule itself. The second is the indirect labeling method in which a bifunctional agent is coupled to the protein and the radiometal is attached to the protein via the bifunctional agent. Various attempts have been made to label antibodies with radiometals by the indirect approach. In one such approach, a chelating agent such as diethylenetriaminepentaacetic acid (DTPA) is conjugated onto the protein and then the metal ion is labeled onto the chelating agent attached to the protein molecule. For example, Khaw et al., *Science* 209: 295–297 (1980) discloses antibodies to cardiac myosin labeled with indium-111 via DTPA and use of the labeled antibodies to image for myocardial infarction. See also, Krejcarek et al., *Biochem. Biophys. Res. Commun.* 77: 581–585 (1977); Childs, R. L. and Hnatowich, O. J., *J. Nucl. Med.* 26: 293 (1985). In a more recent approach, Fritzberg et al. describe the use of particular diamidodithiol and diaminodithiol groups, as chelating agents, Fritzberg et al., *J. Nucl. Med.* 27: 957 (1986).

U.S. Pat. No. 4,659,839 discloses bifunctional coupling agents for joining radionuclide metal ions to biologically useful molecules, including antibody Fab' fragments. The coupling agents contain a maleimide moiety and a paramagnetic or radionuclide chelating moiety. The maleimide is said to selectively bind to free sulfhydryl groups or amine groups. U.S. Pat. No. 4,671,958 discloses methods of attaching linker groups to specific sites on antibodies. Attachment to the antibody is described through sulfhydryl groups of a Fab' or through an oxidized carbohydrate moiety of the Fc region. EPO Publication No. 188,256 discloses proteins conjugated at the lysine amino groups with chelated metal radionuclides for use in vivo. The metal chelating compounds are dithio-diamino or -diamidocarboxylic acids or amines or derivatives thereof. EPO Publication No. 173,629 discloses antibody-metal ion complexes having a metal ion coordinately bound to a compatible chelator covalently bound to an antibody or antibody fragment. Suitable chelators for sulfhydryl attachment are said to include chelators having reactive alkylhalo groups, p-mercuribenzoate groups, and groups capable of Michael-type addition reactions.

Various degrees of success have been achieved with indirect labelling methods. However, the labeled product is often difficult to prepare, has reduced immunoreactivity and is unstable in vivo. Further, techniques for purifying the labeled product before use are often required. A need exists for improved methods of stably labeling proteins for radioimmunodiagnostic and radioimmunotherapeutic procedures, especially with Tc-99m.

SUMMARY OF THE INVENTION

The present invention provides a bifunctional coupling agent for joining a sulfhydryl-containing protein or peptide and a metallic radionuclide. The coupling agent comprises a sulfhydryl selective electrophile, a chelator containing at least one protected thiol and an organic linking radical which serves to join said electrophile and said chelator. The invention further provides a radiodiagnostic precursor comprising an antibody or antibody fragment and the above described bifunctional coupling agent bound to a sulfhydryl group on the antibody or antibody fragment. The invention further provides a radiodiagnostic agent comprising the radiodiagnostic precursor and a metallic radionuclide bound to a thiol group on the precursor.

The invention also provides a method for radiolabelling a protein or peptide having at least one sulfhydryl group. The method comprises contacting the bifunctional coupling agent with the protein or peptide to form a radiodiagnostic precursor. The thiol protecting group(s) are disassociated from the radiodiagnostic precursor and the resulting precursor is contacted with a radiometal.

DETAILED DESCRIPTION OF THE INVENTION

The present sulfhydryl-selective bifunctional coupling agent provides a means of attaching a radionuclide to a protein in a stable fashion. One advantage of the present coupling agent when employed to radiolabel an antibody or antibody fragment is that ligand attachment is removed from the antigen binding region of the antibody or fragment. The sulfhydryl-selective electrophile component of the coupling agent permits site-selective modification of the protein under mild conditions.

Normally, a thiol-containing chelating portion on a bifunctional coupling agent would be incompatible with a sulfhydryl-selective electrophile. It has been found that the chelating moiety of the present coupling agent can be suitably protected from reaction with the electrophile during attachment of the electrophile to a protein substrate. The chelating moiety can be subsequently deprotected to unmask the chelating functionality for radionuclide binding.

The bifunctional coupling agents of the invention can be represented by the general formula E - L - C, wherein E is a sulfhydryl selective electrophile, L is an organic linking radical and C is a chelator containing at least one protected thiol. As used herein, the expression "protected thiol" refers to a thiol chelator masked with a thiol protecting group.

Preferably, the sulfhydryl-selective electrophile is selected from the group consisting of haloalkyl, sulfonate ester, maleimide, and aziridine, and most preferably the group consisting of BrCH$_2$CONH—, ClCH$_2$CONH—, ICH$_2$CONH—and N-substituted maleimide. Suitable organic linking radicals have at least two valancies. Preferred organic linking radicals are selected from the group consisting of linear or branched alkyl, aryl and substituted aryl, heteroaromatic and substituted heteroaromatic, and linear or branched alkyl containing heteroatom substituents for carbon; and optionally contain alkyl, substituted alkyl and heteroatom branching groups. Most preferably, the organic linking radical is —CONHCH$_2$CH$_2$—, —CH$_2$C$_6$H$_4$—, —NHCH$_2$CH$_2$—or —CONHCH(CO$_2$H)CH$_2$CH$_2$CH$_2$CH$_2$—. Suitable chelators contain at least one protected thiol group, and optionally other substituents known to stabilize metal complexes. Such groups and substituents are arranged in a linear or branched manner.

When employed to prepare the radionuclide labeled composition of the invention, the thiol group(s) on the chelating moiety is(are) masked with any organic or inorganic protecting group which can be readily removed under mild conditions to regenerate the free thiol in the presence of a protein without substantially altering the activity of the protein. The chelator can also contain amines, amides, carboxylates, sulfonates and phosphates. In preferred embodiments of the invention, the thiol protecting group is selected from the group consisting of thiol esters, disulfides and Michael-addition products. Most preferably, the protecting group is a thiol ester. Most preferably the chelator is selected from the group consisting of:

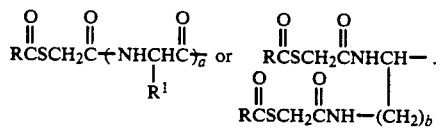

wherein a is an integer from 1 to 5 inclusive, and most preferably 3; b is an integer from 1 to 3 inclusive, and most preferably 1; R is hydrogen, methyl, lower alkyl, hydroxyalkyl, substituted alkyl, alkyl substituted with a functional group, aryl or substituted aryl, and most preferably R is either methyl or phenyl; each R$^1$ is independently hydrogen, methyl, lower alkyl, hydroxyalkyl, substituted alkyl, alkyl substituted with a functional group, aryl or substituted aryl, and most preferably R$^1$ is hydrogen.

Preferred bifunctional coupling agents of the invention are represented by the following formulae:

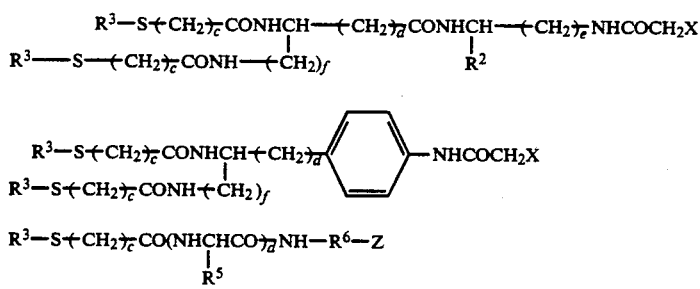

wherein c and f are independently 1, 2, or 3; d and e are independently an integer from 1 to 5, inclusive; X is Cl, Br, or I; R$^2$ is hydrogen, methyl, alkyl, hydroxyalkyl, carboxyalkyl, aryl, substituted aryl, substituted alkyl or alkyl substituted with a functional group; R$^3$ is —COR$^4$ or —SR$^4$ wherein R$^4$ is hydrogen, methyl, alkyl, hydroxyalkyl, carboxyalkyl, aryl, carboxyaryl, substituted aryl, substituted alkyl or alkyl substituted with a functional group; each R$^5$ is independently hydrogen, methyl, alkyl, hydroxyalkyl, carboxyalkyl, aryl, carboxyaryl, substituted aryl, or substituted alkyl; R$^6$ is alkyl, substituted alkyl, —(CH$_2$CH$_2$O)$_g$—CH$_2$CH$_2$—wherein g is an integer from 0 to 5 inclusive, aryl, or substituted aryl; and Z is ClCH$_2$CONH—, BrCH$_2$CONH, ICH$_2$CONH—or

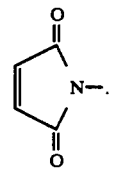

It has been found that bifunctional coupling agents of the invention are useful for binding an antibody with a radiometal having affinity with thiols, such as radionuclides of Tc, Re, Pb and Cu, to prepare radionuclide labeled compositions of the formula Ab - S - E - L - C - M, wherein Ab is an antibody or fragment derived therefrom, S is a sulfhydryl, M is a radiometal having affinity with thiols, and E, L, and C are as defined above.

As stated above, the bifunctional coupling agent can be used to selectively attach a radionuclide to a sulfhydryl-containing group on a protein. Sulfhydryls on proteins are due to the presence of cysteine residues. Other amino acids and functionalities in the protein can be left unmodified. For biologically functional proteins, such as antibodies, modification at a free sulfhydryl is usually distal to the antigen binding sites.

Proteins containing a free sulfhydryl group can be conjugated directly to the bifunctional coupling agent. Many proteins do not possess sulfhydryl groups but do contain disulfide bonds joining cystine amino acids. These disulfide bonds can be reduced to free cysteines by mild reducing agents. Among suitable reducing agents are dithiothreitol, dithioerythritol, cysteine, mercaptoethanol or a variety of other reducing agents. Optimal use of the invention includes the purification of the reduced protein. This purification can be achieved by standard methods, usually by gel filtration chromatography. A representative reduction would be addition of sufficient dithiothreitol to give a 2-20 mM concentration, addition being to a 1-10 mg/mL solution of protein in a buffer at pH 7 to 8. After approximately one hour the protein is passed down a gel filtration column in the buffer desired for reaction with the bifunctional coupling reagent.

In a preferred embodiment, the bifunctional coupling agent is employed to join a radionuclide and an antibody molecule or fragment. Intact antibodies do not normally possess free cysteine, but do contain cystine disulfides. An intact antibody can therefore be joined to the bifunctional coupling agent after reduction as described above. Intact antibodies can also be treated with a proteolytic enzyme, such as pepsin, to give an antigen binding fragment F(ab')₂ and another fragment F_c. The F(ab')₂ can be split into two Fab' fragments by mild reduction. This Fab' contains both an antigen binding site as well as free cysteine sulfhydryl groups. The antigen binding properties of the Fab' are unaffected as the section of the protein comprising the antigen binding site does not react with the bifunctional reagent.

The bifunctional coupling agent is added to the protein solution in an excess relative to the number of free sulfhydryls. Typically to a 1–2 mg/mL solution of protein in a buffer at pH 7 to 8, preferably pH 7.0, is added the bifunctional coupling agent in a co-solvent such as dimethylsulfoxide or dimethylformamide, if required. The agent is present in a 5–15 molar ratio to the number of sulfhydryl groups. If a co-solvent is necessary to solubilize the agent, the concentration of the co-solvent is kept between 1 and 15% v/v, usually around 5%. A reaction time of 1 to 2 hours is generally sufficient to react all of the sulfhydryls present, longer reaction times than this are not optimal. Excess bifunctional coupling agent is then removed. Usually this is accomplished using gel filtration chromatography.

The thiol protecting groups are then removed from the bifunctional coupling agent which is attached to the protein. For the disulfide protected thiols this can be accomplished by the same conditions used to reduce protein disulfides and is described above. Protecting groups which can be removed by retro-Michael reaction need only have the pH of the media increased. The thiol esters can be removed by exposure to reagents generally known to be nucleophilic in neutral aqueous solutions. This can include hydroxide, imidazole, hydrazine and substituted hydrazines and hydroxylamine and substituted hydroxylamines. A typical procedure for the removal of a thiol ester would be to treat a volume of the protein solution with a volume of 0.5–1.0M hydroxylamine at or near pH 7.5 for a period of 5 minutes. The protein can then be purified by gel filtration chromatography.

Deprotection of the bifunctional coupling agent-protein conjugate provides a thiol-containing chelating functionality for the binding of metals, especially radionuclides. The affinity of the deprotected chelating portion for metals is generally high enough that this binding can be accomplished in aqueous solution near neutral pH and at or near ambient temperatures. A pH range of 5–8 and temperatures of 4° to 37° C. can be used.

Some radionuclides require a change in oxidation state prior to complexation with the bifunctional coupling agent. The change in oxidation state can be accomplished either in a separate vessel or in the presence of the bifunctional coupling agent-protein conjugate. Depending on the nature of the radionuclide, and the relative speed of complex formation, a transfer-ligand may be required. This transfer-ligand consists of a molecule or mixture capable of weakly complexing the radionuclide in a reduced state. This transfer ligand is intended only to transiently stabilize an otherwise relatively unstable intermediate. The technetium complex of the bifunctional coupling agent can be prepared in this fashion using D-glucaric acid as a transfer ligand. The eluate from a technetium-99m generator is mixed with an equal volume of 20 to 30 mg/mL monopotassium D-glucaric acid in 0.2N bicarbonate. A reducing agent is then added, usually a 5 uL/mL addition of 5 mg/mL stannous chloride in 0.2N aqueous acetic acid. After waiting an appropriate length of time for the pertechnetate to reduce and the transfer complex to form, the mixture is mixed with the deprotected bifunctional coupling agent-protein conjugate. The protein conjugate is usually in a buffered solution at pH 7 to 8. The mixture is allowed to sit at or near ambient temperature until more than 90 and usually more than 95%, of the technetium becomes attached to the protein. This can be ascertained by a variety of quantitative and qualitative methods including gel filtration HPLC and thin layer chromatography techniques.

The following are examples of most preferred bifunctional coupling agents of the invention.

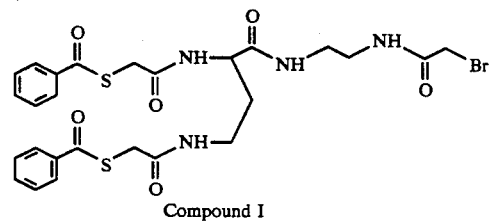
Compound I

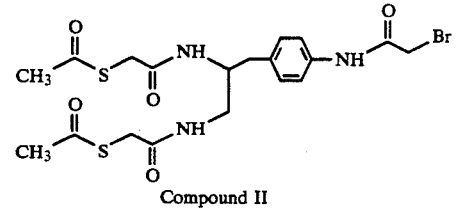
Compound II

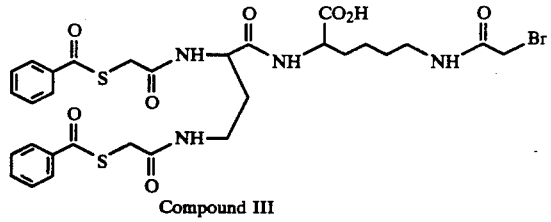
Compound III

Compound I can be readily prepared according to the following scheme:

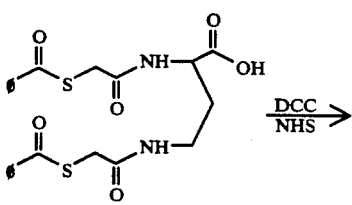

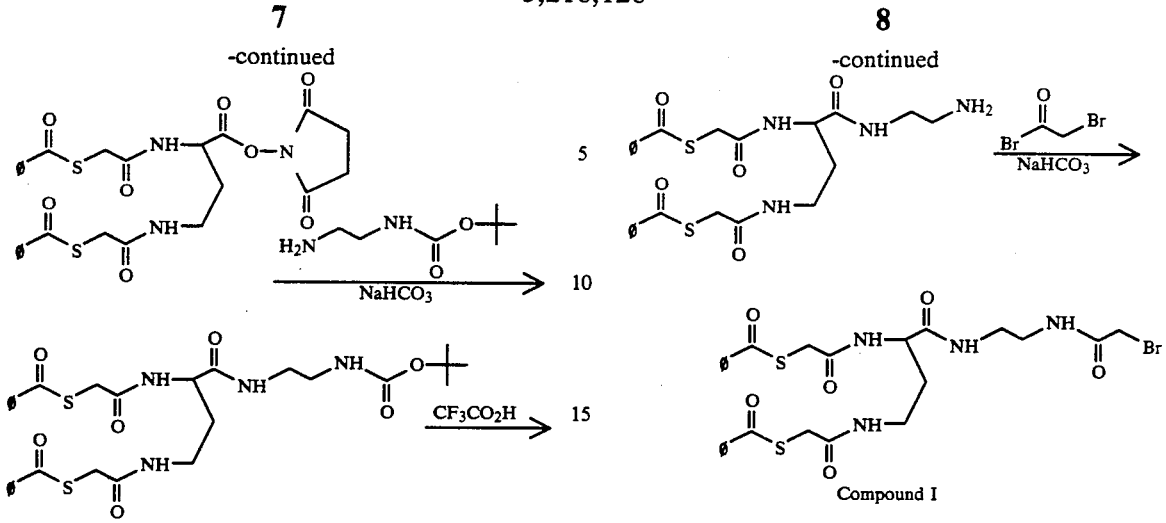
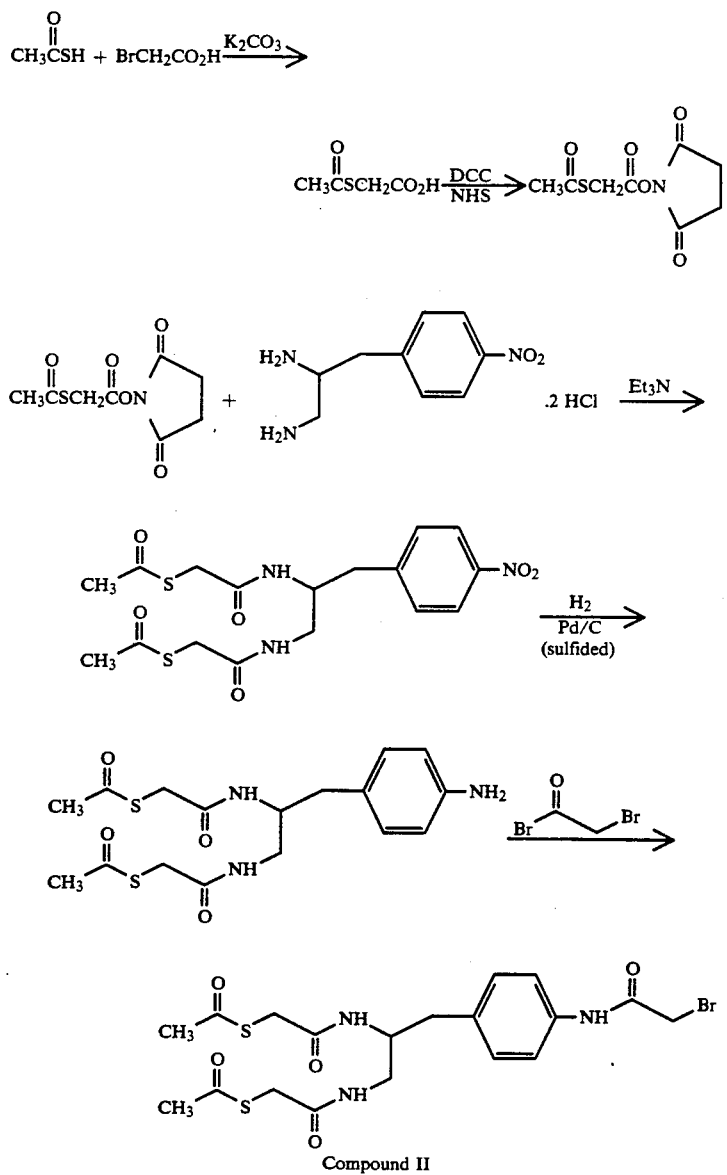
Compound II can be readily prepared according to the following scheme:

Compound III can be readily prepared according to the following scheme:

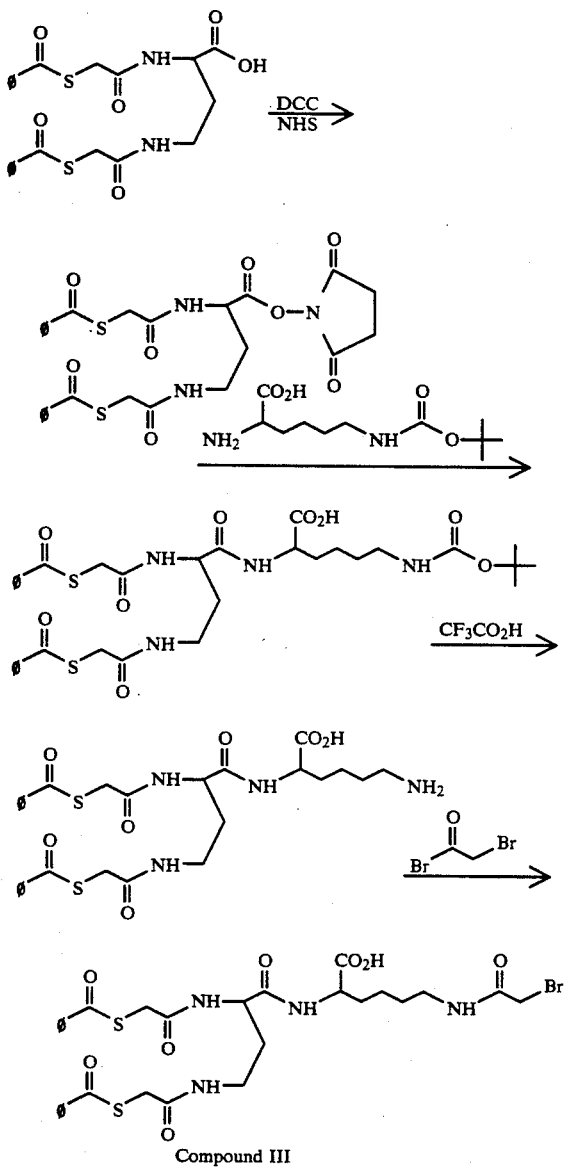

Compound III

The invention is further described in the following examples wherein all parts and percentages are by weight and degrees are Celsius unless otherwise stated.

EXAMPLE I

Preparation of 8,10-bis(2-benzoylthioacetamido)-1-bromo-3.6-diaza-2,7-dioxodecane (Compound I)

a) Preparation of 2,4-bis(2-benzoylthioacetamido)butanoic acid

The above-identified compound was prepared by method described in R. F. Schneider, et al, *J. Nucl. Med.* 25, 223–29 (1984) from dl-2,4-diaminopropanoic acid. The product was recrystallized from acetonitrile/$H_2O$. NMR (DMSO-$d_6$) δ1.78 (m, 1H), 1.94 (m, 1H), 3.16 (m, 2H), 3.81 (s, 2H), 3.89 (s, 2H), 4.26 (m, 1H), 7.36 (m, 4H), 7.69 (t, 2H), 7.94 (m, 4H), 8.22 (br t, 1H, NH), 8.55 (br d, 1H, NH).

b) Preparation of succinimidyl 2,4-bis(2-benzoylthioacetamido)butanoate

To 5.0 g of the acid prepared above (10.54 mmoles) was added 150 mL of THF. The mixture was warmed gently to obtain a clear solution, then cooled to ambient temperature. N-hydroxysuccinimide (1.25 g, 10.86 mmoles, 100 mol %) and dicyclohexylcarbodiimide (2.20 g, 10.66 mmoles, 100 mol %) were added, and the solution stirred at room temperature for 16 h. The precipitated dicyclohexylurea was filtered off, and the filtrate concentrated by rotary evaporator to give a white solid. Recrystallization from 600 mL of 2-propanol gave the succinimidyl ester as a fine white powder. 1.3 g, 2.27 mmoles, 22%. NMR (DMSO-$d_6$) δ1.97 (m, 1H), 2.11 (m, 1H), 2.82 (s, 4H), 3.32 (m, 2H), 3.82 (s, 2H), 3.92 (s, 2H), 4.78 (m, 1H), 7.57 (m, 4H), 7.71 (m, 2H), 7.96 (m, 4H), 8.36 (br t, 1H, NH), 9.01 (br d, 1H, NH).

c) Preparation of 2-(t-butyloxycarbonylaminol)ethylamine.

To a solution of 7.5 g of aminoacetonitrile hydrochloride (81.05 mmoles, 150 mol %) and 10.0 g of NaHCO$_3$ (119 mmoles, 220 mol %) in 150 mL of water was added 11.9 g of di-t-butyl dicarbonate (54.4 mmoles). The heterogenous mixture was stirred vigorously for 16 h at room temperature. The pH was adjusted to 5.0 with 2N HCl. The solution was extracted with ethyl acetate (2×75 mL) and the extracts dried over Na$_2$SO$_4$. Filtration and removal of solvent by rotary evaporator gave a brown oil. Kugelrohr distillation gave a fraction bp 95°, 0.10 mmHg as a low melting white solid. TLC (EtOAc) Rf 0.74, (EtOAc/hexanes 1:1) Rf 0.61. 8.20 g, 52.5 mmoles, 96%. In a Parr pressure bottle was placed 2.0 g of the above protected nitrile and 75 mL of glacial acetic acid. After the protected nitrile had dissolved, 0.20 g of 5% Pd/C was added and the mixture hydrogenated at 45 psig H$_2$ for 2h. The mixture was filtered through acid-washed celite, and the acetic acid removed by rotary evaporator (30°, vacuum pump) to give a tan oil.

d) Preparation of 3-aza-4-oxo-5,7-bis(2-benzoylthioacetamido)-1-(t-butyloxycarbonylaminol)heptane Succinimidyl 2,4-bis(2-benzoylthioacetamido)-butanoate above (2.41 g, 4.22 mmoles) was suspended in 40 mL of H$_2$O. To this suspension was added crude 2-(t-butyloxycarbonylamino)ethylamine (prepared from 1.32 g of t-butyloxycarbonylaminoacetonitrile as above, 100 mol%) in 40 mL of THF. To this mixture was added 5 mL of saturated NaHCO$_3$ in water. The heterogenous mixture was stirred for 3h at room temperature. An additional 20 mL of saturated NaHCO$_3$ was added, and the mixture extracted with EtOAc (2×100 mL). The extracts were dried over Na$_2$SO$_4$, filtered and the solvent removed by rotary evaporator to give a yellow oil. This was triturated with 10 mL of ethyl acetate and filtered. The filtrate was purified on 40 g of silica gel, eluting with ethyl acetate. 100 mg, 0.16 mmoles, 4%. TLC (EtOAc) Rf 0.10. NMR (MeOH-d4) δ1.40 (s, 9H), 1.86 (m, 1H), 2.08 (m, 1H), 3.18 (m, 4H), 3.80 (s, 2H), 3.86 (s, 2H), 4.38 (m, 1H), 7.49 (m, 4H), 7.65 (m, 2H), 7.96 (m, 4H). Two protons (C-7) obscured by solvent.

e) Preparation of 3-aza-5,7-bis(2-benzoylthioacetamido)-4-oxo-1-heptaneamine trifluoroacetate The above 3-aza-5,7-bis(2-benzoylthioacetamido)-4-oxo-1-(t-butyloxycarbonylamino)heptane (60 mg, 0.097 mmoles) was deprotected by dissolving in 5 mL of trifluoroacetic acid and stirring at ambient temperature for 1 h. Removal of the trifluoroacetic acid (rotary evaporator, followed by drying under vacuum 16 h) gave a pale yellow glass. NMR (MeOH-$d_4$) $\delta$1.91 (m, 1H), 2.12 (m, 1H), 3.10 (m, 2H), 3.53 (m, 2H), 3.61 (m, 2H), 3.86 (s, 2H), 3.93 (s, 2H), 4.34 (m, 1H), 7.49 (m, 4H), 7.72 (m, 2H), 7.95 (m, 4H).

f) Preparation of 8.10-bis(2-benzoylthioacetamido)-1-bromo-3,6-diaza-2,7-dioxodecane (Compound I)

The amine trifluoroacetate described above (60 mg, 0.10 mmoles) was dissolved in 5 mL of water. To this solution was added 50 mg of $NaHCO_3$ (0.60 mmoles, 600 mol %) and 20 uL of bromoacetyl bromide (0.22 mmoles, 230 mol %). The slightly brown mixture was stirred for 1 h at ambient temperature. Water (10 mL) and saturated $NaHCO_3$ (10 mL) was added, and the mixture extracted with chloroform (2×50 mL). The extracts were dried over $Na_2SO_4$, filtered and the solvent removed by rotary evaporator to a yellow oil. This solidified on drying under vacuum. NMR ($CDCl_3$) $\delta$1.91 (m, 1H), 1.98 (m, 1H), 3.41 (m, 4H), 3.59 (m, 2H), 3.74 (s, 2H), 3.78 (s, 2H), 3.80 (s, 2H), 4.48 (m, 1H), 7.19 (br m, 1H, N$\overline{H}$), 7.31 (br m, 1H, NH), 7.42 (br m, 1H, NH), 7.47 (m, 4H), 7.61 (m, 2H), 7.95 (m, 4H).

EXAMPLE 2

Coupling of 8,10-bis(2-benzoylthioacetamido)-1-bromo-3,6-diaza-2,7-dioxodecane (Compound I) to Antimyosin a) Coupling of Compound I Antimyosin to Antimyosin Fab' and Deprotection of the S-benzoyls Antimyosin F(ab')$_2$ (Centocor Lot #01057, 0.40 mL, 10 mg/mL) pH 7.0 in 0.10M Tris buffer was added to 80 uL of 9.26 mg/mL dithiothreitol (DTT) in 0.10M phosphate pH 7.0. The mixture was mixed gently, then left at room temperature for 1 h. The Fab' was purified by Sephadex G-25 (medium) chromatography (1×18 cm), eluting with 0.10M phosphate pH 7.0 containing 1 mM EDTA. Fractions (1.0 mL) were collected and analyzed for protein concentration by $E^{0.1\%}=1.4$. Aliquots of each fraction (100 uL) were removed and diluted to 1.0 mL with 0.10 M phosphate pH 8.0. To these dilutions were added 50 uL of 5 mg/mL 5,5'-dithiobis(2-nitrobenzoic acid) (DTNB, Ellman's reagent) in 0.10M phosphate pH 8.0. The DTNB solutions were mixed, and $A_{412}$ measured after 15 minutes. Equivalents of sulfhydryl were determined from a molar absorption coefficient of 15,800 at 412 nm and a protein MW of 50,000. Found: fraction 5, 0.57 mg/mL, 2.2 sulfhydryl/mole; fraction 6, 1.56 mg/mL, 2.7 sulfhydryl/mole; fraction 7, 1.37 mg/mL, 2.8 sulfhydryl/mole. Fractions 5-7 were combined and treated with 0.35 mL of 2.4 mg/mL Compound I in DMF. This solution was $5.1\times10^5$M sulfhydryl on protein, $5.0\times10^{-4}$M Compound I and 15% v/v DMF. The cloudy solution was gently mixed, then left at room temperature for 1 h. The reaction was concentrated on a Centricon filtration apparatus (10,000 MW cutoff) at 5000 rpm for 75 min, giving 0.8 mL of solution. This was purified by Sephadex G-25 (medium) chromatography (1×14 cm), eluting with 0.10M phosphate pH 6.5 containing 1 mM EDTA. Fractions (1.0 mL) were collected and analyzed for protein concentration $A_{280}$. As a chromophore had been added to the protein, the $A_{280}$ readings gave only qualitative information. Aliquots (100 uL) of each fraction were diluted to 1.0 mL with 0.10M phosphate pH 8.0 and treated with DTNB as above. No fraction had an $A_{412}$ greater than 0.005. Fraction 6 had $A_{280}=1.96$.

To 0.50 mL of fraction 6 of the Compound I- Antimyosin conjugate was added 0.50 mL of 1.0M $NH_2OH$ Hl in 0.5M HEPES, pH 7.5 (adjusted with 50% NaOH). The solution was gently mixed, then left at room temperature for 5 min. The mixture was purified by Sephadex G-25 (medium) chromatography (1×14 cm), eluting with 0.10M phosphate pH 6.5 containing 1 mM EDTA. Fractions (1.0 mL) were collected and analyzed for protein concentration by using $E^{0.1\%}=1.4$. Aliquots (100 uL) of each fraction were diluted to 1.0 mL with 0.10M phosphate pH 8.0 and treated with DTNB as above. Found: fraction 5, 0.17 mg/mL, 2.5 sulfhydryl/mole; fraction 6, 0.28 mg/mL, 2.4 sulfhydryl/mole.

EXAMPLE 3

Technetium Labeling of Antimyosin Modified With Compound I

Sodium [Tc-99m]pertechnetate solution from a Mo-99/Tc-99m generator was diluted to 4.0 mCi/mL with saline. To 0.5 mL of this solution was added 0.5 mL of 26 mg/mL D-glucaric acid, mono-potassium salt in 0.2N $NaHCO_3$, followed by 20 uL of 5 mg/mL $SnCl_2$ in 0.2N acetic acid. The solution was mixed, then left at room temperature for 5 min. To an aliquot (100 uL) of the deprotected Antimyosin-Compound I conjugate (Fraction 6 above, 0.028 mg protein) was added 100 uL of the [Tc-99m]technetium-glucarate solution. This was mixed gently, then left at room temperature for 1h.

Chromatography on Whatman 3MM paper eluted with acetonitrile/water 60/40 showed a single peak at the origin. ITLC (Gelman) in saline showed 98% of radioactivity in the bottom half of the plate; Tc-glucarate on ITLC in saline showed 99% in the top half. HPLC showed 7.3% of the radioactivity at Rt 9.96 [F(ab')2] and 91.6% at Rt 11.05 [F(ab')]. For the affinity chromatography column 4.5 uL of the labeled protein was diluted to 1.0 mL with phosphate buffered saline/bovine serum albumin (PBS/BSA) solution and 100 was uL applied to the column. The radioactivity eluting with 10×1 mL of PBS/BSA was collected and counted in a gamma counter (unbound fractions). The column was then eluted with 10×1 mL of 0.10M glycine pH 2.5 and the fractions counted (bound fractions). Found: unbound 17,725 cpm; bound 963,594 cpm; 98.2% immunoreactive.

EXAMPLE 4

Biodistribution of Radiolabed Antimyosin-With Compound I Conjugate

Biodistribution of the radiolabeled Antimyosin Fab' was determined in mice. An aliquot of the labeled protein solution was diluted to 1 mCi/mL, filtered through a 0.2 um membrane filter, and 0.10 mL injected into each mouse. At various time points, the mice (n=3)

were sacrificed and the organs counted. The data is given in Table 1.

An aliquot of the labeled protein was mixed with an equal volume of fresh human serum and incubated at 37°. At various time points a portion was removed and analyzed by gel filtration HPLC. The results are presented in Table 3.

TABLE 1

Biodistribution of Technetium - 99 m Labeled Antimyosin - Compound I Conjugate in Mice

| Organ | % dose/gram | | |
|---|---|---|---|
| | 1 h | 6 h | 24 h |
| Blood | 8.0 | 1.6 | 0.5 |
| Heart | 2.5 | 0.7 | 0.2 |
| Lung | 3.9 | 0.9 | 0.4 |
| Liver | 3.8 | 2.2 | 1.2 |
| Kidneys | 69.4 | 42.5 | 23.2 |

EXAMPLE 5

Preparation of 1-(4-(2-bromoacetamido)phenylmethyl)-1,2-bis(2-acetylthioacetamido)ethane) (Compound III a) Preparation of 2-acetylthioacetic acid

To a mixture of thiolacetic acid (7.2 mL, 0.1 mol) and $K_2CO_3$ (41 g, 0.3 mol) in acetone (350 mL) was added bromoacetic acid (13.8 g, 0.1 mol). The mixture was stirred at room temperature for two days. The solvent was removed under reduced pressure and the residue was taken up in water (100 mL) and acidified with conc. HCl. The mixture was extracted with ethyl acetate (3×) and the combined organic extracts were washed with brine and dried ($Na_2SO_4$). Removal of solvent under reduced pressure gave an oil which was Kugelrohr distilled to give the acid (9.2 g, 69%). Bp 110°-130° at 0.5 mmHg. NMR, ($CDCl_3$) δ2.41 (s, 3H), 3.75 (s, 2H).

b) Preparation of succinimidyl 2-acetylthioacetate

A solution of 2-acetylthioacetic acid (9.1 g, 0.068 mol) and N-hydroxysuccinimide (8.6 g, 0.075 mol) in ethyl acetate (250 mL) was treated dropwise with a solution of dicyclohexylcarbodiimide (15.7 g, 0.076 mol) in ethyl acetate (50 mL). After stirring at room temperature for 1.5 hours, the mixture was kept at 4° overnight. The precipitated urea was removed by filtration and the filtrate was concentrated under reduced pressure. The crude product was recrystallized from ethyl acetate to yield the succinimidyl ester (9.4 g, 60%). Mp 93°-95°. NMR, ($CDCl_3$) δ2.42 (s, 3H), 2.83 (s, 4H), 3.98 (s, 2H).

c) Preparation of 1-(4-nitrophenylmethyl)-1,2-bis(2-acetylthioacetacetamido)ethane To a mixture of 1-p-nitrobenzylethylenediamine dihydrochloride, (Gansow, O, et al. *Inorg. Chem.* 25, 2772 (1986)), (2.7 g, 0.01 mol) and triethylamine (2.2 g, 0.022 mol) in dimethoxyethane (50 mL) was added the succinimidyl ester above (5.1 g, 0.022 mol). After stirring overnight the mixture was poured into water (150 mL). After stirring 20 minutes the product was collected by filtration and recrystallized from methanol to provide the product (3.1 g, 73%). Mp 169°-171°. NMR (DMSO-$d_6$) δ2.28 (s, 3H), 2.31 (s, 3H), 2.77 (2H,m), 3.11 (2H,m), 3.46 (s,2H), 3.57 (s,2H), 3.98 (1H,m), 7.41 (2H,d), 7.98 (1H,d), 8.10 (2H,d), 8.13(1H,t).

d) Preparation of 1-(4-aminophenylmethyl)-1,2-bis(2-acetylthioacetamido)ethane The p-nitrobenzyl compound prepared above (1.56 g, 3.6 mmoles) was dissolved in methanol (150 mL) by warming. The cooled solution was treated with sulfided 5%Pd/C, 50% moisture (Englehart 0.70 g) and hydrogenated on a Parr apparatus at 50 psi $H_2$. After four hours the reaction was not complete by TLC ($SiO_2$, 10% $CH_3OH/CHCl_3$). Additional catalyst (0.3 g) was added and the hydrogenation was continued for an additional 2 ¼ hours, after which 20 all the starting material was consumed. The mixture was stored under $N_2$ overnight. The catalyst was removed by filtration through celite and the solvent removed under reduced pressure. The resulting oil was flash chromatographed ($SiO_2$, $CHCl_3$-3% $CH_3OH/CHCl_3$ gradient). Fractions containing pure product were combined and evaporated to give the aniline as an oil (0.77 g, 53%). NMR ($CDCl_3$) δ2.51 (s, 3H), 2.55 (s, 3H), 2.81 (2H,m), 3.42 (2H,m), 3.63 (2H,d), 3.67 (2H,s), 3.85 (2H,s), 4.24 (1H,m), 6.67 (1H,d), 6.75 (2H,d), 6.82 (1H,t), 7.08 (2H,d).

e) Preparation of 1-(4-(2-bromoacetamidolphenylmethyl)-1,2-bis(2-acetylthioacetamido)ethane Solutions of the aniline prepared above (0.2 g, 0.5 mmoles) in $CHCl_3$ (2 mL), $NaHCO_3$ (0.17 g, 2 mmoles) in water (4 mL), and bromoacetyl bromide (0.2 g, 1 mmoles) in $CHCl_3$ (2 mL) were prepared and cooled in an ice bath. The acid bromide was added to the $NaHCO_3$ solution followed by dropwise addition of the aniline. After 30 minutes the mixture was diluted with water and $CHCl_3$ and the organic layer was separated and washed with water, brine and dried ($NaSO_4$). Removal of solvent under reduced pressure gave the bromoacetyl derivative II as a glass (0.17 g, 65%). MMR (DMSO-$d_6$) δ2.46 (s, 3H), 2.48 (s, 3H), 2.73 (2H,m) 3.22 (2H,m), 3.62 (s,2H), 3.70 (s,2H), 4.04 (1H,m), 4.14 (s,2H), 7.24 (2H,d), 7.58 (2H,d), 8.05 (1H,d), 8.23 (1H,t), 10.32 (1H,s).

EXAMPLE 6

Conjugation of compound II with Antimyosin Fab'

Antimyosin Fab' (0.950 mL, 2.2 mg/mL; 2.7 sulfhydryls per Fab' via Ellman's assay) was treated with a solution of the p-bromoacetamido ligand II (4.3 uL of $5.7 \times 10^{-3}$ g in 40 uL DMF). After one hour the protein was purified by Sephadex G-25 chromatography (1×10 cm) with 50 mM phosphate, 1 mM EDTA, pH 7.5 buffer, 1 mL fractions were collected. The presence of the aromatic nucleus of the ligand interfered with the absorbance at 280 nm, so an accurate assessment of protein concentration could not be made. No sulfhydryls were detected by Ellman's assay.

A 0.5 mL sample of the Antimyosin-Compound II-conjugate (approximately 1.9 mg/mL) was treated with hydroxylamine hydrochloride (0.5 mL of 1 M in 0.5M HEPES, pH 7.5). After 5 minutes the solution was purified by Sephadex G-25 chromatography (1×10 cm) using 50 mM phosphate, 1 mM EDTA, pH 6.5 buffer, 1 mL fractions were collected. Fraction 5 (0.6 mg/mL) was found to contain 2.3 sulfhydryls per Fab' by Ellman's assay.

EXAMPLE 7

Technetium-99m Labeling of Antimyosin-Compound II Conjugate

A solution of [Tc-99m]pertechnetate (0.5 mL, 2 mCi) was treated with a solution of potassium glucarate (0.5 mL of 26 mg in 1 mL of 0.2M NaHCO$_3$) followed by 40 uL of SnCl$_2$ (8.8 mg in 3.5 mL of 0.1M acetic acid). After 5 minutes, 0.5 mL of the resulting [Tc-99m]Tc-glucarate solution was mixed with the deprotected Antimyosin - Compound II conjugate above (0.5 mL). The resulting solution was 0.25 mg/mL protein at 1 mCi/mL (4 mCi/mg). After 30 minutes paper chromatography (60/40, CH$_3$CN/H$_2$O) indicated 97% of the radioactivity was protein bound. This was confirmed by HPLC.

A portion of the above solution (0.8 mL) was diluted to 4 mL with saline and passed through a 0.22 um filter. This was used for mouse biodistribution. The dose per mouse was 0.1 mL (5 ug at 20 mCi per mouse).

TABLE 2

Tc-99 m Labeled Antimyosin-Compound II Mouse biodistribution of Conjugate

| Organ | 30 min | 2.5 hours | 18 hours |
|---|---|---|---|
| | % dose/gram | | |
| Blood | 18.9 (3.5) | 6.7 (0.9) | 0.8 (0.1) |
| Heart | 3.7 (0.6) | 1.7 (0.2) | 0.4 (0.1) |
| Lung | 5.8 (1.0) | 2.9 (0.6) | 0.6 (0.2) |
| Liver | 7.4 (1.4) | 5.6 (0.9) | 2.6 (0.3) |
| Spleen | 2.9 (0.4) | 1.7 (0.2) | 0.9 (0.3) |
| Kidneys | 31.0 (4.4) | 27.0 (4.7) | 11.3 (1.5) |
| Stomach | 1.2 (0.2) | 1.2 (0.2) | 0.3 (0.1) |
| G.I. | 2.1 (0.4) | 3.0 (0.5) | 0.5 (0.1) |
| Muscle | 0.7 (0.3) | 0.4 (0.1) | 0.2 (0.1) |
| | % dose/organ | | |
| Blood | 37.2 (7.1) | 12.8 (1.4) | 1.4 (0.1) |
| Heart | 0.5 (0.1) | 0.2 (0.0) | 0.1 (0.02) |
| Lung | 1.2 (0.3) | 0.5 (0.1) | 0.1 (0.0) |
| Liver | 10.8 (0.9) | 7.1 (0.6) | 4.0 (0.3) |
| Spleen | 0.3 (0.1) | 0.1 (0.04) | 0.1 (0.0) |
| Kidneys | 11.9 (1.4) | 10.5 (1.7) | 4.1 (0.4) |
| Stomach | 0.3 (0.1) | 0.3 (0.1) | 0.1 (0.0) |
| G.I. | 6.6 (0.6) | 8.0 (1.1) | 1.5 (0.3) |
| Muscle | 8.9 (4.1) | 5.3 (0.6) | 2.5 (0.5) |

Standard deviations given in parentheses

TABLE 3

Serum Stability of Technetium - 99 m Labeled Fab' Fragments at 37°

| | % Protein Bound by HPLC | |
|---|---|---|
| Time | Compound I - Modified Antimyosin | Compound II - Modified Antimyosin |
| 1 h | 72.3 | 93 |
| 24 h | 54.9 | 75 |

EXAMPLE 8 a) Preparation of 1,3-bis(2-benzoylthioacetamido)-13-bromo-5,11-diaza-4,12-dioxo-6-carboxytridecane Succinimidyl 2,4-bis(2-benzoylthioacetamido) benzoate (3.63g, 6.35 mmoles) was suspended in 29 mL of THF. To this was added 25 mL of H$_2$O, 1.60 g of NaHCO$_3$ (19.05 mmoles, 300 mol %) and 1.56 g of N$^ε$-t BOC-L-Lysine (6.33 mmoles, 100 mol %). The heterogenous mixture was stirred for 3 h at room temperature. The reaction was extracted with EtOAc (2×75 mL) and the extracts discarded. The aqueous layer was cooled to 0°, and the pH adjusted to 3.0 with 2N HCl. The acidified solution was extracted with EtOAc (2×100 mL) and the extracts dried over Na Filtration and removal of solvent gave a yellow oil. This was purified by chromatography on 100 g of silica gel, eluting with chloroform/2-propanol 19:1. 1.0 g, 1.42 mmoles, 22%. NMR (MeOH-d$_4$) δ1:42 (s)+1.50 (m) (15H, should be 13), 1.99 (m, 4H), 3.80 (s, 2H), 3.90 (s), 4.40–4.60 (three separate m, 2H total) 7.50 (m, 2H), 7.65 (m, 2H), 7.85 (m, 2H), 7.97 (m, 4H). 2H obscured by solvent signal.

b) Preparation of 5-aza-1,3-bis(2-benzoylthioacetamido)-6-carboxy-4-oxodecaneamine trifluoroacetate The lysine derivative prepared above (0.54 g, 0.77 mmoles) was treated with 10 mL of trifluoroacetic acid for 1 h and the trifluoroacetic acid removed in vacuo.

c) Preparation of 1,3-bis(2-benzoylthioacetamido)-13-bromo-5,11-diaza-4,12-dioxo-6-carboxytridecane The crude amine trifluoroacetate prepared above (0.77 mmoles) was suspended in 30 mL of H$_2$O, addition of 10 mL of dimethylformamide dissolved most of the gel. To this mixture was added 0.26 g of NaHCO$_3$ (3.10 mmoles, 400 mol %) and 100 uL of bromoacetyl bromide (1.15 mmoles, 150 mol %). The solution became homogeneous after 15 min. The reaction was stirred for 1 h at room temperature. Water (60 mL) was added and the pH adjusted to 4.0. The acidified solution was extracted with EtOAc (2×75 mL). The combined extracts were washed with 1M NaH$_2$PO$_4$ (4×50 mL), then dried over Na$_2$SO$_4$. Filtration and removal of solvent by rotary evaporator gave a yellow oil. This oil was dried under vacuum for 16 h to give 0.20 g (36% of theoretical).

What is claimed is:

1. A bifunctional coupling agent having the formula:

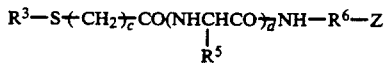

wherein c is independently 1, 2, or 3; d is independently an integer from 1 to 5; R$^3$ is —COR$^4$ or —SR$^4$ wherein R$^4$ is hydrogen or methyl, R$^5$ is independently hydrogen or methyl, R$^6$ is —(CH$_2$CH$_2$O)$_g$—CH$_2$CH$_2$—wherein g is an integer from 0 to 5 inclusive; and Z is ClCH$_2$CONH—, BrCH$_2$CONH, ICH$_2$CONH—or

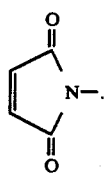

* * * * *